United States Patent
Cowley et al.

(10) Patent No.: US 12,414,793 B2
(45) Date of Patent: Sep. 16, 2025

(54) DEVICES, SYSTEMS, AND METHODS OF MANUFACTURING FLUID-COOLED ULTRASONIC SURGICAL INSTRUMENTS

(71) Applicant: Covidien LP, Mansfield, MA (US)

(72) Inventors: Matthew S. Cowley, Frederick, CO (US); David J. Van Tol, Boulder, CO (US); Michael B. Lyons, Boulder, CO (US)

(73) Assignee: Covidien LP, Mansfield, MA (US)

( * ) Notice: Subject to any disclaimer, the term of this patent is extended or adjusted under 35 U.S.C. 154(b) by 957 days.

(21) Appl. No.: 17/541,951

(22) Filed: Dec. 3, 2021

(65) Prior Publication Data

US 2022/0211408 A1    Jul. 7, 2022

Related U.S. Application Data

(60) Provisional application No. 63/134,268, filed on Jan. 6, 2021.

(51) Int. Cl.
*A61B 17/32*    (2006.01)
*A61B 17/00*    (2006.01)

(52) U.S. Cl.
CPC .......... *A61B 17/320092* (2013.01); *A61B 2017/00526* (2013.01); *A61B 2017/32007* (2017.08);
(Continued)

(58) Field of Classification Search
CPC ........ A61M 25/00; A61B 17/29; A61B 17/32; A61B 2018/0005; A61B 17/320068; A61B 2017/32007; A61B 17/320092; A61B 2017/320074; A61B 2017/00526; A61B 2217/007

See application file for complete search history.

(56) References Cited

U.S. PATENT DOCUMENTS

| 3,589,363 A | 6/1971 | Banko et al. |
| 4,016,882 A | 4/1977 | Broadwin et al. |

(Continued)

FOREIGN PATENT DOCUMENTS

| EP | 3061415 A1 | 8/2016 | |
| WO | 2019168634 A1 | 9/2019 | |
| WO | WO-2023139529 A1 * | 7/2023 | ..... A61B 17/320092 |

OTHER PUBLICATIONS

Extended European Search Report issued in corresponding European Application No. 22150452.5 dated May 13, 2022, 8 pages.

*Primary Examiner* — Ashley L Fishback

(57) ABSTRACT

An ultrasonic surgical system includes a waveguide defining first and second longitudinal lumens extending through at least a portion of a length of the waveguide. A distal transverse lumen is defined within the waveguide transversely through at least a portion of the waveguide to intersect and interconnect the first and second longitudinal lumens. First and second proximal transverse lumens extend from first and second proximal transverse apertures within the waveguide transversely through portions of the waveguide to intersect the first and second longitudinal lumens, respectively. Inflow and outflow conduits are fluidly coupled with the first and second proximal transverse apertures, respectively, to enable the inflow of fluid into the first longitudinal lumen and the outflow of fluid from the second longitudinal lumen, respectively.

19 Claims, 10 Drawing Sheets

(52) U.S. Cl.
CPC ............ *A61B 2017/320074* (2017.08); *A61B 2217/007* (2013.01)

(56) References Cited

U.S. PATENT DOCUMENTS

| | | | |
|---|---|---|---|
| 4,223,676 A | 9/1980 | Wuchinich et al. |
| 4,587,958 A | 5/1986 | Noguchi et al. |
| 4,660,573 A | 4/1987 | Brumbach |
| 4,681,561 A | 7/1987 | Hood et al. |
| 4,724,834 A | 2/1988 | Alperovich et al. |
| 4,754,760 A | 7/1988 | Fukukita et al. |
| 4,832,022 A | 5/1989 | Tjulkov et al. |
| 4,832,683 A | 5/1989 | Idemoto et al. |
| 5,076,276 A | 12/1991 | Sakurai et al. |
| 5,163,433 A | 11/1992 | Kagawa et al. |
| 5,188,102 A | 2/1993 | Idemoto et al. |
| 5,205,817 A | 4/1993 | Idemoto et al. |
| 5,211,625 A | 5/1993 | Sakurai et al. |
| 5,221,282 A | 6/1993 | Wuchinich |
| 5,261,922 A | 11/1993 | Hood |
| 5,358,505 A | 10/1994 | Nuchinich |
| 5,383,876 A | 1/1995 | Nardella |
| 5,391,144 A | 2/1995 | Sakurai et al. |
| 5,419,761 A | 5/1995 | Narayanan et al. |
| 5,462,522 A | 10/1995 | Sakurai et al. |
| 5,486,162 A | 1/1996 | Brumbach |
| 5,496,342 A | 3/1996 | Urich |
| 5,560,362 A | 10/1996 | Sliwa, Jr. et al. |
| 5,624,393 A | 4/1997 | Diamond |
| 5,797,931 A | 8/1998 | Bito et al. |
| 5,830,192 A | 11/1998 | Van Voorhis |
| 5,879,363 A | 3/1999 | Urich |
| 5,906,628 A | 5/1999 | Miyawaki et al. |
| 6,073,492 A | 6/2000 | Rosselson et al. |
| 6,120,519 A | 9/2000 | Weber et al. |
| 6,206,876 B1 | 3/2001 | Levine et al. |
| 6,315,215 B1 | 11/2001 | Gipson et al. |
| 6,379,371 B1 | 4/2002 | Novak et al. |
| 6,380,264 B1 | 4/2002 | Jameson et al. |
| 6,383,183 B1 | 5/2002 | Sekino et al. |
| 6,443,969 B1 | 9/2002 | Novak et al. |
| 6,454,781 B1 | 9/2002 | Witt et al. |
| 6,551,337 B1 | 4/2003 | Rabiner et al. |
| 6,633,234 B2 | 10/2003 | Wiener et al. |
| 6,764,487 B2 | 7/2004 | Mulier et al. |
| 6,770,071 B2 | 8/2004 | Woloszko et al. |
| 6,810,585 B2 | 11/2004 | Hickok |
| 6,923,421 B2 | 8/2005 | Raftis |
| 6,939,350 B2 | 9/2005 | Phan |
| 7,074,219 B2 | 7/2006 | Levine et al. |
| 7,273,483 B2 | 9/2007 | Wiener et al. |
| 7,404,816 B2 | 7/2008 | Abboud et al. |
| 7,530,986 B2 | 5/2009 | Beaupre et al. |
| 7,572,268 B2 | 8/2009 | Babaev |
| 8,348,880 B2 | 1/2013 | Messerly et al. |
| 8,546,996 B2 | 10/2013 | Messerly et al. |
| 8,628,534 B2 | 1/2014 | Jones et al. |
| 8,641,609 B2 | 2/2014 | Hestad et al. |
| 8,641,658 B1 | 2/2014 | Banko |
| 8,974,478 B2 | 3/2015 | Ross et al. |
| 9,044,261 B2 | 6/2015 | Houser |
| 9,113,930 B2 | 8/2015 | Reid, Jr. |
| 9,113,943 B2 | 8/2015 | Ross et al. |
| 9,211,137 B2 | 12/2015 | Voic |
| 9,271,751 B2 | 3/2016 | Houser et al. |
| 9,276,300 B2 | 3/2016 | Mueller |
| 9,320,528 B2 | 4/2016 | Voic et al. |
| 9,387,005 B2 | 7/2016 | Voic |
| 9,622,767 B2 | 4/2017 | Stoddard et al. |
| 9,655,641 B2 | 5/2017 | Stoddard et al. |
| 9,737,735 B2 | 8/2017 | Dietz et al. |
| 9,764,166 B2 | 9/2017 | Stoddard et al. |
| 9,839,410 B2 | 12/2017 | Courtney et al. |
| 10,342,566 B2 | 7/2019 | Stoddard et al. |
| 10,368,897 B2 | 8/2019 | Uhlrich et al. |
| 2002/0087157 A1 | 7/2002 | Sliwa et al. |
| 2002/0091404 A1 | 7/2002 | Beaupre |
| 2003/0181904 A1 | 9/2003 | Levine et al. |
| 2003/0204199 A1 | 10/2003 | Novak et al. |
| 2004/0087972 A1 | 5/2004 | Mulholland et al. |
| 2005/0209578 A1 | 9/2005 | Christian Evans et al. |
| 2006/0195106 A1 | 8/2006 | Jones et al. |
| 2006/0265035 A1 | 11/2006 | Yachi et al. |
| 2007/0162050 A1 | 7/2007 | Sartor |
| 2007/0233054 A1 | 10/2007 | Babaev |
| 2008/0015563 A1 | 1/2008 | Hoey et al. |
| 2008/0058845 A1 | 3/2008 | Shimizu et al. |
| 2008/0281200 A1 | 11/2008 | Voic et al. |
| 2009/0036914 A1 | 2/2009 | Houser |
| 2009/0306550 A1 | 12/2009 | Babaev |
| 2010/0274236 A1 | 10/2010 | Krimsky |
| 2010/0298743 A1 | 11/2010 | Nield et al. |
| 2012/0253371 A1 | 10/2012 | Ross et al. |
| 2013/0072950 A1 | 3/2013 | Ross et al. |
| 2013/0085490 A1 | 4/2013 | Kerr |
| 2013/0090576 A1 | 4/2013 | Stulen et al. |
| 2013/0178842 A1 | 7/2013 | Reid, Jr. |
| 2013/0184729 A1 | 7/2013 | Yasunaga |
| 2013/0324917 A1 | 12/2013 | Akagane |
| 2014/0135804 A1 | 5/2014 | Weisenburgh et al. |
| 2014/0276369 A1 | 9/2014 | Banko |
| 2014/0276740 A1 | 9/2014 | Larson et al. |
| 2015/0005771 A1 | 1/2015 | Voic |
| 2015/0005774 A1 | 1/2015 | Voic |
| 2015/0005775 A1 | 1/2015 | Voic |
| 2015/0073457 A1 | 3/2015 | Stoddard et al. |
| 2015/0073458 A1 | 3/2015 | Stoddard et al. |
| 2015/0088137 A1 | 3/2015 | Manna |
| 2015/0148834 A1 | 5/2015 | Gee et al. |
| 2015/0165240 A1 | 6/2015 | Stoddard et al. |
| 2015/0297255 A1 | 10/2015 | Fan et al. |
| 2016/0082292 A1 | 3/2016 | Kudo |
| 2016/0089155 A1 | 3/2016 | Lark et al. |
| 2016/0129285 A1 | 5/2016 | Mikus et al. |
| 2016/0143657 A1 | 5/2016 | Estera et al. |
| 2016/0143658 A1 | 5/2016 | Stokes et al. |
| 2016/0143659 A1 | 5/2016 | Glutz et al. |
| 2016/0144204 A1 | 5/2016 | Akagane |
| 2016/0195450 A1 | 7/2016 | Akagane |
| 2017/0281215 A1 | 10/2017 | Stoddard et al. |
| 2017/0325886 A1 | 11/2017 | Graham et al. |
| 2019/0247073 A1 | 8/2019 | Cowley |

\* cited by examiner

DEVICES, SYSTEMS, AND METHODS OF MANUFACTURING FLUID-COOLED ULTRASONIC SURGICAL INSTRUMENTS

CROSS-REFERENCE TO RELATED APPLICATIONS

This application claims the benefit of, and priority to, U.S. Provisional Patent Application No. 63/134,268 filed on Jan. 6, 2021, the entire contents of which are hereby incorporated herein by reference.

FIELD

The present disclosure relates to ultrasonic surgical instruments and, more particularly, to devices, systems, and methods of manufacturing fluid-cooled ultrasonic surgical instruments.

BACKGROUND

Ultrasonic surgical instruments and systems utilize ultrasonic energy, i.e., mechanical vibration energy transmitted at ultrasonic frequencies, to treat, e.g., seal and/or transect, tissue. Ultrasonic surgical instruments typically include a waveguide having a transducer coupled to a proximal end portion of the waveguide and an end effector disposed at a distal end portion of the waveguide. The waveguide transmits the ultrasonic energy produced by the transducer to the end effector for treating tissue at the end effector. The end effector may include a blade, hook, ball, etc. and/or other features such as a clamping mechanism for clamping tissue against the end effector and/or to facilitate manipulating tissue. During use, the waveguide and/or end effector of an ultrasonic surgical instrument can reach temperatures greater than 200° C. or even 300° C.

SUMMARY

As used herein, the term "distal" refers to the portion that is described which is further from an operator (whether a human surgeon or a surgical robot), while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, and/or other variations, up to and including plus or minus 10 percent. Further, any or all of the aspects described herein, to the extent consistent, may be used in conjunction with any or all of the other aspects described herein.

Provided in accordance with aspects of the present disclosure is an ultrasonic surgical system including an ultrasonic waveguide body defining first and second longitudinal lumens extending through at least a portion of a length of the ultrasonic waveguide body. A distal transverse lumen is defined within the ultrasonic waveguide body transversely through at least a portion of the ultrasonic waveguide body to intersect and interconnect the first and second longitudinal lumens. A first proximal transverse lumen extends from a first proximal transverse aperture within the ultrasonic waveguide body transversely through a portion of the ultrasonic waveguide body to intersect the first longitudinal lumen. A second proximal transverse lumen extends from a second proximal transverse aperture within the ultrasonic waveguide body transversely through a portion of the ultrasonic waveguide body to intersect the second longitudinal lumen. Inflow and outflow conduits are fluidly coupled with the first and second proximal transverse apertures, respectively, to enable the inflow of fluid into the first longitudinal lumen and the outflow of fluid from the second longitudinal lumen, respectively.

In an aspect of the present disclosure, the distal transverse lumen extends from a distal transverse aperture and a distal transverse aperture plug closes the distal transverse aperture to inhibit escape of fluid therethrough.

In an aspect of the present disclosure, the first and second longitudinal lumens extend proximally from first and second distal face apertures defined within a distal face of the ultrasonic waveguide body. In such aspects, at least one distal face aperture plug closes the first and second distal face apertures to inhibit escape of fluid therethrough.

In another aspect of the present disclosure, the first and second proximal transverse apertures are defined on opposed sides of the ultrasonic waveguide body. Alternatively, the first and second proximal transverse apertures may be defined on the same side of the ultrasonic waveguide body.

In still another aspect of the present disclosure, first and second proximal transverse aperture plugs form a seal between the inflow and outflow conduits and the first and second proximal transverse apertures, respectively.

In yet another aspect of the present disclosure, the ultrasonic surgical system further includes a proximal waveguide body adapted to connect to an ultrasonic transducer. In such aspects, the ultrasonic waveguide body is a distal waveguide body including a blade and extends distally from the proximal waveguide body. The distal waveguide body may be releasably engagable with the proximal waveguide body or permanently affixed (or formed with) the proximal waveguide body. Engagement of the proximal and distal waveguide bodies, in aspects where such engagement is provided, may close proximal ends of the first and second longitudinal lumens.

In still yet another aspect of the present disclosure, the waveguide body includes a base and a blade extending distally from the base. The blade may define opposed narrow surfaces and opposed broad surfaces. At least a portion of the distal transverse lumen may be disposed within 10% of a length of the blade from a distal end of the blade.

In another aspect of the present disclosure, the ultrasonic surgical system further includes a cooling system configured to pump cooling fluid through the inflow conduit into the first longitudinal lumen and/or pump cooling fluid through the second longitudinal lumen into the outflow conduit.

In another aspect of the present disclosure, the ultrasonic surgical system further includes a housing supporting the cooling system and an elongated assembly extending distally from the housing. The elongated assembly includes the ultrasonic waveguide body.

In yet another aspect of the present disclosure, the housing further supports an ultrasonic transducer configured to produce ultrasonic energy for transmission along the ultrasonic waveguide body. The housing may further still support an ultrasonic generator configured to produce an ultrasonic drive signal for driving the ultrasonic transducer, and/or a battery configured to power the ultrasonic generator.

In another aspect of the present disclosure, the distal transverse lumen is at least partially formed via a distal cap defining a distal tip of the distal waveguide body.

A method of manufacturing an ultrasonic surgical system provided in accordance with the present disclosure includes forming first and second longitudinal lumens through at least a portion of a length of an ultrasonic waveguide body, forming a distal transverse lumen transversely through at least a portion of the ultrasonic waveguide body to intersect and interconnect the first and second longitudinal lumens, forming first and second proximal transverse lumens transversely through a portion of the ultrasonic waveguide body to intersect the first and second longitudinal lumens, respectively, plugging apertures formed from the forming of the first and second longitudinal lumens, and plugging an aperture formed from the forming of the distal transverse lumen.

In an aspect of the present disclosure, the method further includes fluidly connecting an inflow conduit with the first proximal transverse aperture and/or fluidly connecting an outflow conduit with the second proximal transverse aperture.

In another aspect of the present disclosure, the method further includes attaching the ultrasonic waveguide body, as a distal waveguide body, to a proximal waveguide body. Such attaching may close proximal ends of the first and second longitudinal lumens. The distal waveguide body may be attached to the proximal waveguide body via inertial friction welding or in any other suitable manner.

In still another aspect of the present disclosure, the method further includes coupling the first and second proximal transverse lumens with inflow and outflow conduits, respectively, associated with a cooling system.

In another aspect of the present disclosure, forming the distal transverse lumen includes securing a cap to a distal end of the ultrasonic waveguide body to define a distal tip of the ultrasonic waveguide body.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
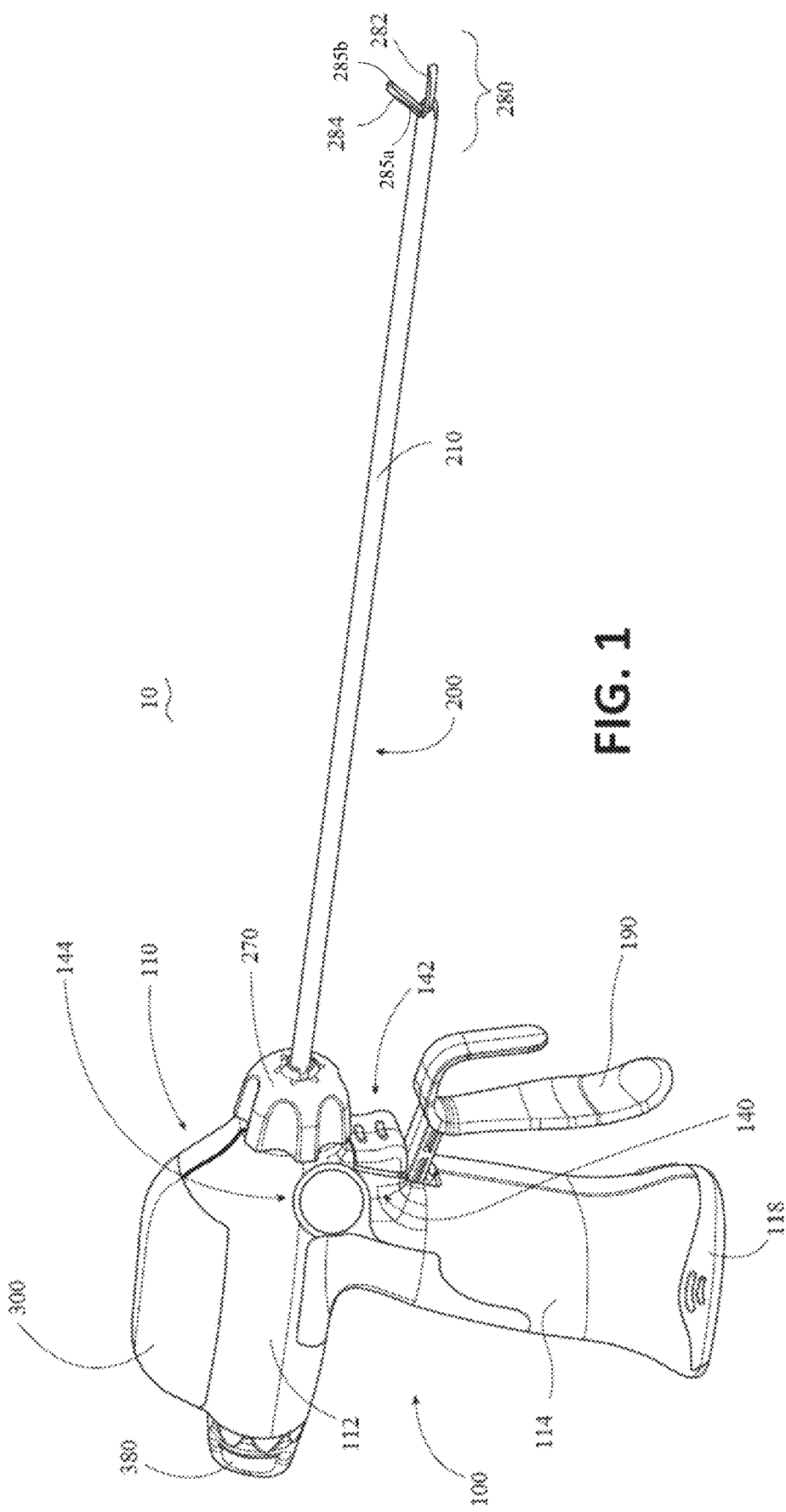
FIG. 1 is a perspective view of an ultrasonic surgical instrument provided in accordance with the present disclosure.
Figure 2:
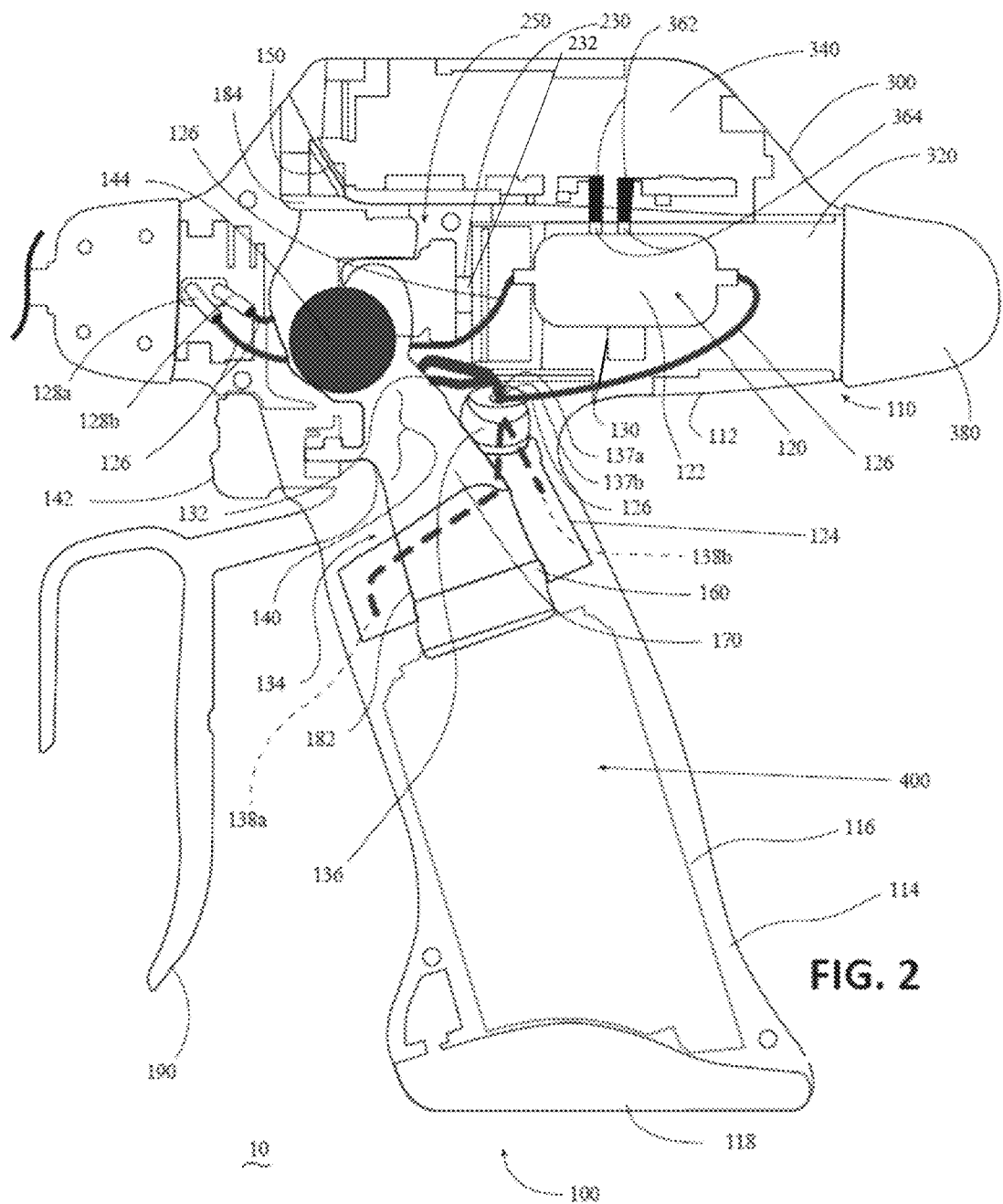
FIG. 2 is a side, cut-away view of a proximal portion of the ultrasonic surgical instrument of FIG. 1.
Figure 3:
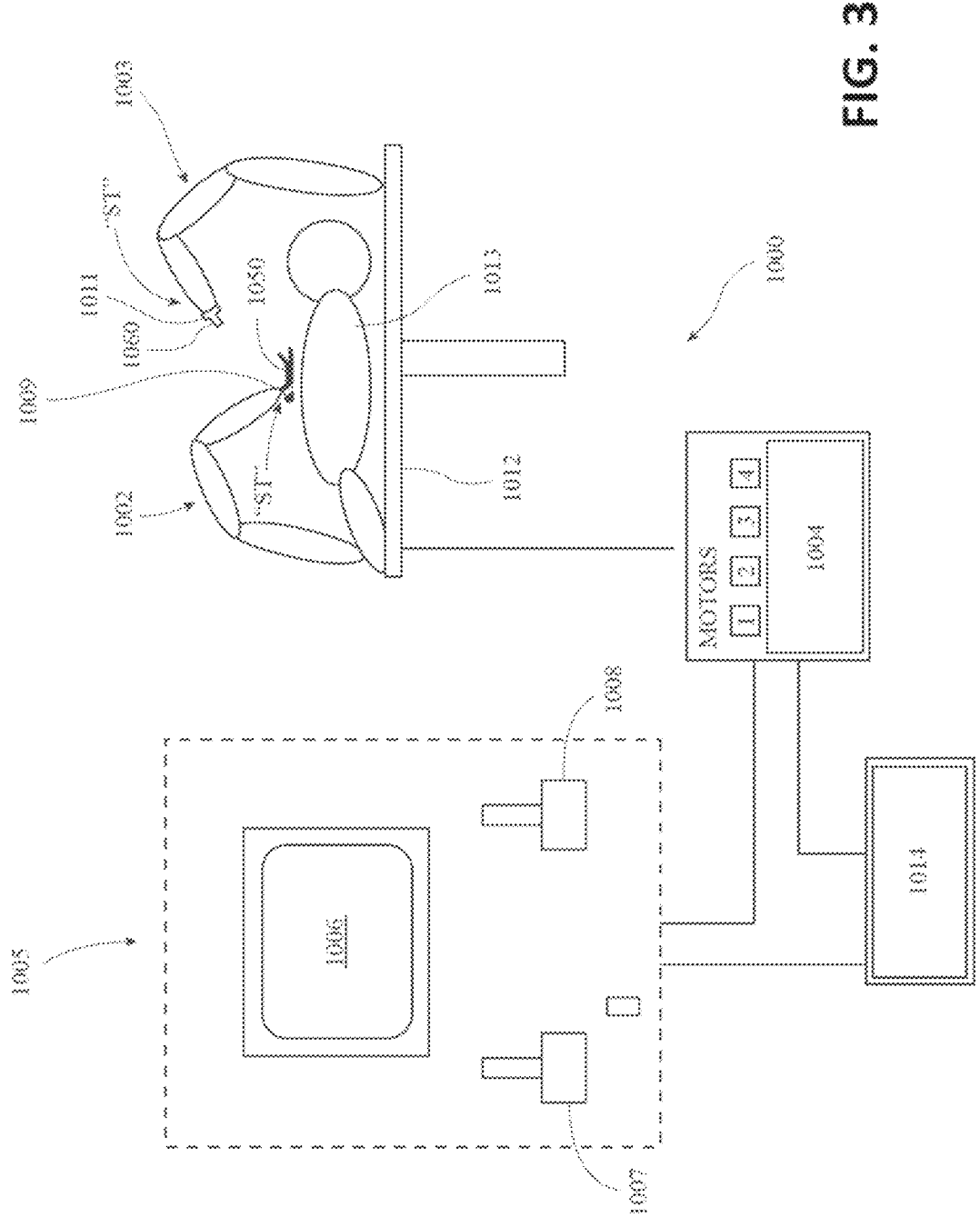
FIG. 3 is a schematic illustration of a robotic surgical system provided in accordance with the present disclosure.

Turning to FIGS. 1 and 2, an ultrasonic surgical instrument provided in accordance with aspects of the present disclosure is generally identified by reference numeral 10. Instrument 10 is a fully cordless instrument that incorporates an on-board cooling system in addition to an on-board power source, e.g., battery, and an ultrasonic generator and transducer. However, it is also contemplated that instrument 10 be configured as a corded instrument, e.g., wherein instrument 10 is configured to connect to a remote cooling system by way of one or more fluid lines and to a remote ultrasonic generator (separate from or integrated with the remote cooling system) by way of a cable; or as a partially-corded instrument, e.g., wherein instrument 10 includes an on-board power source and ultrasonic generator and is configured to connect to a remote cooling system by way of one or more fluid lines, or wherein instrument 10 incorporates an on-board cooling system and is configured to connect to a remote ultrasonic generator. Likewise, other style ultrasonic instruments are also contemplated such as, for example, pencil-style instruments, hemostat-style instruments, etc. Thus, although particular aspects and features of instrument 10 are detailed below, it is understood that the aspects and features of the present disclosure are equally applicable for use with any other suitable ultrasonic surgical instrument or system, e.g., robotic surgical system 1000 (FIG. 3). Other suitable instruments for use in accordance with the present disclosure including remote or on-board cooling systems are described, for example, in Patent Application Pub. No. US 2019/0247073, titled "REMOVABLE FLUID RESERVOIR AND ULTRASONIC SURGICAL INSTRUMENT INCLUDING THE SAME" and filed on Feb. 13, 2018, and Patent Application Pub. No. US 2017/0281215, titled "DEVICES, SYSTEMS, AND METHODS FOR COOLING A SURGICAL INSTRUMENT" and filed on Mar. 18, 2017, the entire contents of each of which are hereby incorporated herein by reference.

Instrument 10 generally includes a handle assembly 100, an elongated assembly 200 that extends distally from handle assembly 100, a transducer and generator assembly ("TAG") 300 configured for releasable engagement with handle assembly 100, and a battery 400 configured for removable receipt within handle assembly 100. Elongated assembly 200 may be integral with handle assembly 100 or may be releasably engagable with handle assembly 100.

Handle assembly 100 includes a housing 110, a cooling system 120, a switch assembly 140, a generator dock 150, a battery dock 160, a flex circuit assembly 170 (including flex circuit portions 182, 184), and a clamp trigger 190.

Housing 110 of handle assembly 100 defines a body portion 112 defining a longitudinal axis and a fixed handle portion 114 extending from body portion 112 at an oblique angle relative to the longitudinal axis of body portion 112 (although fixed handle portion 114 may alternatively extend perpendicularly relative to the longitudinal axis of body portion 112). Body portion 112 of housing 110 is configured to receive a proximal portion of elongated assembly 200 in operable engagement with clamp trigger 190 such that actuation of clamp trigger 190 manipulates end effector assembly 280 of elongated assembly 200. When engaged with body portion 112 of housing 110, elongated assembly 200 is aligned on the longitudinal axis of body portion 112.

Body portion 112 of housing 110 is also configured to support TAG 300 thereon with transducer 320 of TAG 300 mechanically coupled with waveguide 230 of elongated assembly 200, e.g., via a threaded connection, latching, or in any other suitable manner, and both aligned on the longitudinal axis of body portion 112 of housing 110. Generator 340 of TAG 300 is electrically coupled with generator dock 150 of housing 110 when TAG 300 is engaged with body portion 112 of housing 110. Fixed handle portion 114 of housing 110 defines an internal compartment 116 configured to removably receive battery 400 therein and a hinged door 118 configured to enclose battery 400 within internal component 116.

Cooling system 120 includes one or more fluid pumps 122 and, in some aspects, a fluid reservoir 124, although fluid reservoir 124 may be omitted in other configurations. Cooling system 120 further includes associated tubing 126 operably interconnecting fluid pump 122, fluid reservoir 124, and inflow and return conduits 128a, 128b (or interconnecting fluid pump 122 and inflow and return conduits 128a, 128b, in aspects where fluid reservoir 124 is omitted) for pumping cooling fluid to and returning cooling fluid from elongated assembly 200. Inflow and return conduits 128a, 128b may extend along and/or through elongated assembly 200, ultimately entering waveguide 230 thereof to permit circulation of cooling fluid through blade 282 of end effector assembly 280 of elongated assembly 200, as described in greater detail below.

The one or more fluid pumps 122 of cooling system 120 are supported within body portion 112 of housing 110. For example, a fluid pump 122 may be supported on either or both sides of body portion 112 of housing 110 at radially-spaced positions relative to the longitudinal axis of body portion 112 of housing 110. In such a configuration, fluid pumps 122 may define relatively thin, elongate configurations such that sufficient space is defined between the pumps 122 and/or the pump 122 and housing 110 to permit passage of transducer 320 of TAG 300 therebetween (in alignment on the longitudinal axis) while requiring minimal, if any, increase in the overall with dimension of body portion 112 of housing 110 to accommodate pump(s) 122.

A connection interface 130 of cooling system 120 for enabling power and/or control signals to be transmitted to pump(s) 122 is positioned so as not to interfere with TAG 300. Further, a connector 132, e.g., lead wire, cable, flex circuit, or other suitable connector, extends through body portion 112 of housing 110 to couple the connection interface 130 with flex circuit assembly 170 of handle assembly 100 to permit communication of power and control signals between pump(s) 122, generator 340, switch assembly 140, and/or battery 400. More specifically, pump(s) of cooling system 120 may be controlled via a controller of generator 340, battery 400, or a separate controller of cooling system 120, e.g., within control box 130. Regardless of the location and/or configuration, the controller is configured to control pump(s) 122 so as to maintain a flow of cooling fluid sufficient to cool blade 282 of end effector 280, to activate and deactivate cooling in response to manual inputs, and/or to implement automatic cooling (for example, upon deactivation of the supply of energy). The one or more fluid pumps 122 may be piezoelectric microfluidic pumps or other microfluidic pumps such as micro-peristaltic pumps, syringe pumps, etc. Regardless of the particular pump configuration utilized, the one or more fluid pumps 122 may, in aspects, be configured to generate sufficient flow rate of cooling fluid so as to cool waveguide 230 of elongated assembly 200 from an initial temperature of about 300° C. to about 100° C. (or about 120° C.) to a cooled temperature of about 70° C. to about 0° C. (or less than about 60° C.) in from about 0.5 seconds to about 2.5 seconds (or in less than about 2 seconds). However, other temperatures and/or cooling times are also contemplated.

Continuing with reference to FIGS. 1 and 2, fluid reservoir 124 is disposed within housing 110 of handle assembly 100. More specifically, fluid reservoir 124 is disposed within fixed handle portion 114 of housing 110 and is positioned between internal compartment 116 of fixed handle portion 114 and body portion 112 of housing 110. Fluid reservoir 124 may define a cut-out 134 within which at least a portion of clamp trigger 190 extends upon actuation thereof. As such, fluid reservoir 124 does not interfere with actuation of clamp trigger 190. It is also contemplated that fluid reservoir 124 be positioned in other locations, e.g., at a free end of fixed handle portion 114 such that battery 400 is disposed between fluid reservoir 124 and body portion 112.

Fluid reservoir 124 further includes a port 136 having an input 137a and an output 137b. Tubing 126 of cooling system 120 is coupled to input 137a and output 137b of fluid reservoir 124 to couple fluid reservoir 124 with fluid pump(s) 122 and inflow and return conduits 128a, 128b. More specifically, either or both of the ends 138a, 138b of the tubes of tubing 126 may extend through input 137a and output 137b and into fluid reservoir 124 such that the ends 138a, 138b of the tubes of tubing 126 are disposed at opposite sides, ends, or portions of fluid reservoir 124, thereby maximizing the spacing therebetween. This configuration inhibits the hotter, returned cooling fluid from being immediately pumped back out of fluid reservoir 124. Further, the ends 138a, 138b of the tubes of tubing 126 are positioned within fluid reservoir 124 relative to one another such that, regardless of the orientation of handle assembly 100, any air in fluid reservoir 124 is inhibited from entering inflow conduit 128a.

Switch assembly 140 of handle assembly 100 includes an energy activation button 142 operably positioned to electrically couple to flex circuit assembly 170. Flex circuit assembly 170 electrically couples switch assembly 140, battery 400, and TAG 300 with one another. Thus, when energy activation button 142 is activated in an appropriate manner, power is supplied from battery 400 to TAG 300. Energy activation button 142 may be configured for dual-mode activation such that, a first activation of energy activation button 142 drives TAG 300 in a "LOW" power mode, while a second, different activation of energy activation button 142 drives TAG 300 in a "HIGH" power mode. Other suitable activation configurations are also contemplated.

Switch assembly 140 of handle assembly 100 further includes, in aspects, a pair of cooling activation buttons 144 operably positioned on either side of housing 110. Flex circuit assembly 170 electrically couples connection interface 130 of cooling system 120 with switch assembly 140, battery 400, and TAG 300. Thus, activation of either or both of cooling activation buttons 144 initiates cooling. In aspects, multiple activations and/or particular activation patterns of cooling activation button(s) 144 may subsequently terminate cooling, switch between different cooling modes or programs, etc.

Generator dock 150 is disposed on body portion 112 of housing 110 and is positioned to electrically couple to generator 340 of TAG 300 upon engagement of TAG 300 with housing 110. Battery dock 160 is disposed within internal compartment 116 of fixed handle portion 114 of housing 110 and is positioned to electrically couple to battery 400 upon receipt of battery 400 within internal compartment 116. Docks 150, 160, flex circuit assembly 170 (including flex circuit portions 182, 184 thereof), and connector 132 of cooling system 120 electrically couple TAG 300, switch assembly 140, control box 130 of cooling system 120, and battery 400 with one another to enable communication of power and/or control signals therebetween. Flex circuit portion 182, more specifically, interconnects battery dock 160 with flex circuit assembly 170. The flexible configuration of flex circuit portion 182 enables routing of flex circuit 182 about fluid reservoir 124, which is disposed between flex circuit assembly 170 and battery dock 160. Flex circuit portion 184, on the other hand, electrically couples flex circuit assembly 170 with generator dock 150.

Referring still to FIGS. 1 and 2, clamp trigger 190 of handle assembly 100 of instrument 10 extends from body portion 112 of housing 110 in opposing relation relative to fixed handle portion 114 of housing 110. Clamp trigger 190 is pivotably coupled to body portion 112 of housing 110 and operably associated with elongated assembly 200 such that pivoting of clamp trigger 190 towards fixed handle portion 114 of housing 110 pivots jaw 284 of end effector assembly 280 of elongated assembly 200 from an open position to a clamping position for clamping tissue between jaw 284 and blade 282, which extends distally from waveguide 230 of elongated assembly 200.

Elongated assembly 200 generally includes a sleeve assembly having an outer sleeve 210 and an inner sleeve (not shown) disposed within outer sleeve 210, waveguide 230 extending through the inner sleeve (not shown), a drive assembly 250, a rotation assembly 270 operably disposed about outer sleeve 210, and end effector assembly 280 disposed at the distal end of the sleeve assembly. End effector assembly 280 includes, as noted above, blade 282 and jaw 284, which is operably coupled to outer sleeve 210 such that translation of outer sleeve 210 pivots jaw 284 relative to blade 282 between the open and clamping positions. Drive assembly 250 operably couples a proximal portion of outer sleeve 210 with clamp trigger 190 such that actuation of clamp trigger 190 pivots jaw 284 relative to blade 282 between the open and clamping positions. In the above-detailed configuration, the inner sleeve is a support sleeve and the outer sleeve is a drive sleeve, although the opposite configuration is also contemplated, as are other suitable drive mechanisms for pivoting jaw 284 relative to blade 282.

Jaw 284 of end effector assembly 280 includes a more-rigid structural body 285a and a more-compliant jaw liner 285b. Structural body 285a is pivotably coupled to the inner sleeve of elongated assembly 200 and operably coupled with outer sleeve 210 of elongated assembly 200 to enable the above-detailed translation of outer sleeve 210 to impart pivotal motion of jaw 284 relative to blade 282 to clamp tissue between jaw liner 285b of jaw 284 and blade 282. Jaw liner 285b is positioned to oppose blade 282 in the clamping position of jaw 284.

Waveguide 230 extends through the inner sleeve (not shown), includes blade 282 extending from the distal end thereof and includes a proximal end portion that is configured to operably couple to transducer 320, e.g., via a threaded connection, latching, or in any other suitable manner. Inflow and return conduits 128a, 128b, in aspects, may extend from housing 110 at least partially along and/or through elongated assembly 200 before fluidly coupling with an interior flow path defined within waveguide 230 or may fluidly couple with waveguide 230 within housing 110. Waveguide 230, the interior flow path defined within waveguide 230, and the connection of inflow and return conduits 128a, 128b to waveguide 230 are described in greater detail below.

TAG 300 and battery 400 are each removable from handle assembly 100 to facilitate disposal of handle assembly 100 or to enable sterilization of handle assembly 100. TAG 300 may be configured to withstand sterilization such that TAG 300 may be sterilized for repeated use. Battery 400, on the other hand, is configured to be aseptically transferred and retained within compartment 116 of fixed handle portion 114 of housing 110 of handle assembly 100 such that battery 400 may be repeatedly used without requiring sterilization thereof. Alternatively or additionally, battery 400 may be sterilized. In some configurations, TAG 300 (or a portion thereof, e.g., generator 340 or transducer 320) may be integral with housing 110.

TAG 300 includes ultrasonic transducer 320 and generator 340. A set of connectors 362 and corresponding rotational contacts 364 associated with generator 340 and ultrasonic transducer 320, respectively, enable data and drive signals to be communicated from generator 340 to transducer 320, e.g., the piezoelectric stack of transducer 320, to drive transducer 320. Battery 400 powers generator 340 to produce a drive signal, e.g., a high voltage AC signal, that is communicated to transducer 320. Transducer 320 converts the signal into mechanical motion that is output along waveguide 230 to blade 282 of end effector assembly 280. Transducer 320 further includes a rotation knob 380 disposed at a proximal end thereof to enable rotation of transducer 320 relative to generator 340 and handle assembly 100. Rotation knob 380 may also facilitates operable coupling of transducer 320 with elongated assembly 200.

With reference to FIG. 3, a robotic surgical system in accordance with the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, a surgical tool "ST" supporting an end effector 1050, 1060. One of the surgical tools "ST" may be ultrasonic surgical instrument 10 (FIG. 1), wherein manual manipulation and actuation features are replaced with robotic inputs. In such configurations, robotic surgical system 1000 may include or be configured to connect to an ultrasonic generator, a power source, and cooling system. The other surgical tool "ST" may include any other suitable surgical instrument, e.g., an endoscopic camera, other surgical tool, etc. Robot arms 1002, 1003 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and, thus, the surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Referring to FIGS. 1, 2, 4A, 4B, waveguide 230, as noted above, includes blade 282 disposed at a distal end thereof. Waveguide 230, more specifically, includes a proximal body 232 (FIGS. 2 and 4A) and a distal body 234 (FIGS. 4A and 4B) that includes blade 282. In aspects, proximal body 232 and distal body 234 may be integrally formed from a single piece of material or may be separately formed and subsequently attached to one another (permanently or removably). Proximal body 232 and distal body 234 may, in aspects where proximal and distal body 232, 234 are separately formed and subsequently attached, be attached via threaded engagement, e.g., via receipt of a threaded plug 233 (FIG. 4A) of proximal body 232 within a threaded bore 236 (FIGS. 4A and 4B) defined within a proximal end of distal body 234. Other methods of attachment are also contemplated, such as various types of welding (e.g., inertial friction welding), brazing, soldering, diffusion bonding, etc. Proximal body 232 and/or distal body 234 may be formed from aluminum, aluminum alloy, titanium, a titanium alloy, or other suitable similar or different material(s).

Proximal body 232 of waveguide 230 extends from housing 110 through at least a portion of the inner support sleeve of elongated assembly 200 to distal body 234. Proximal body 232 is configured to operable engage ultrasonic transducer 320 such that ultrasonic motion produced by ultrasonic transducer 320 is transmitted along proximal body 232 to distal body 234 and, ultimately, blade 282 for treating tissue clamped between blade 282 and jaw 284 or positioned adjacent to blade 282. Proximal body 232 may define a generally cylindrical-shaped configuration and may be solid, although hollow or semi-hollow configurations are also contemplated.

Figure 4A:
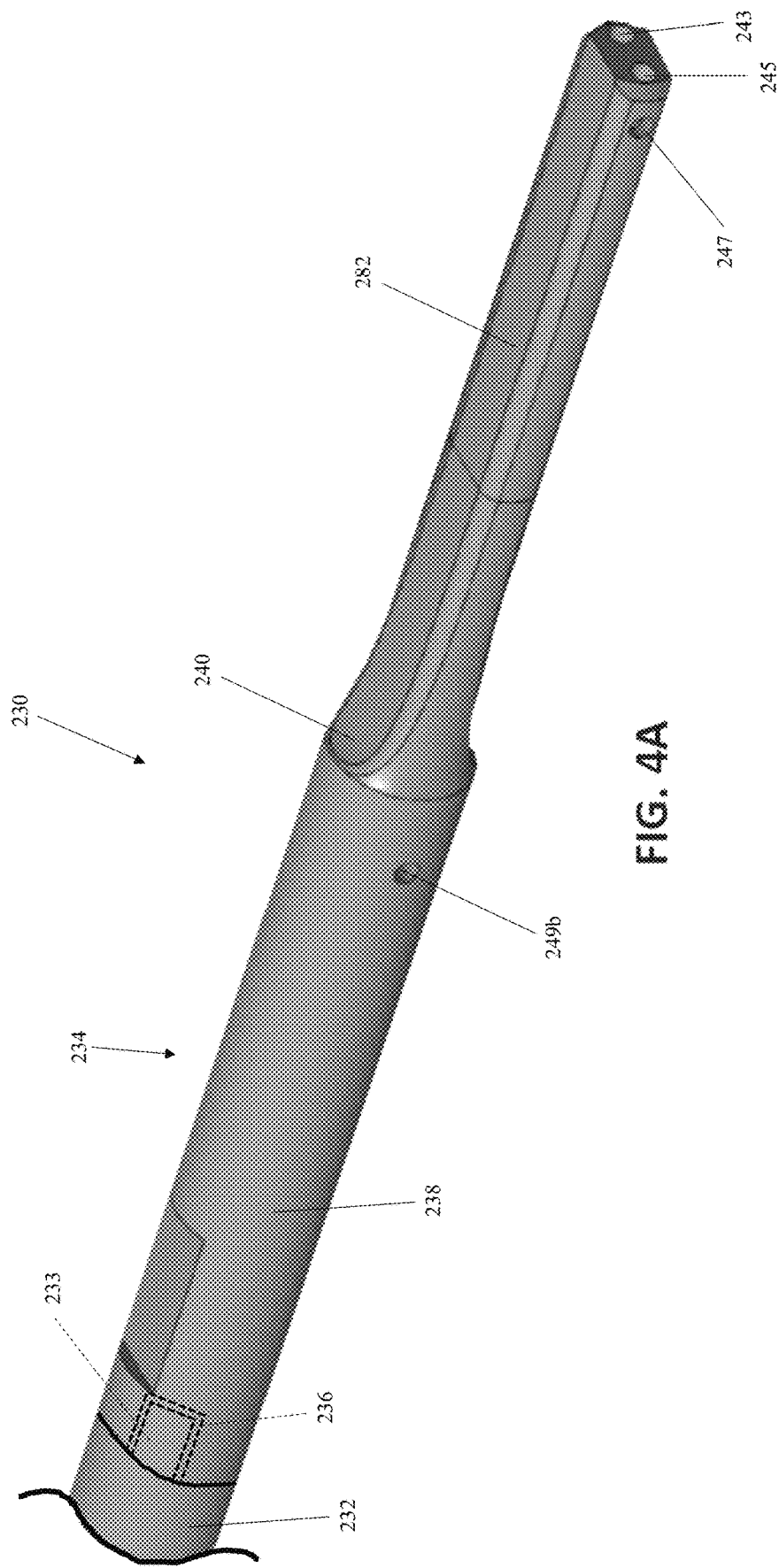
FIG. 4A is an enlarged, perspective view of a distal portion of a waveguide of the ultrasonic surgical instrument of FIG. 1.
Figure 4B:
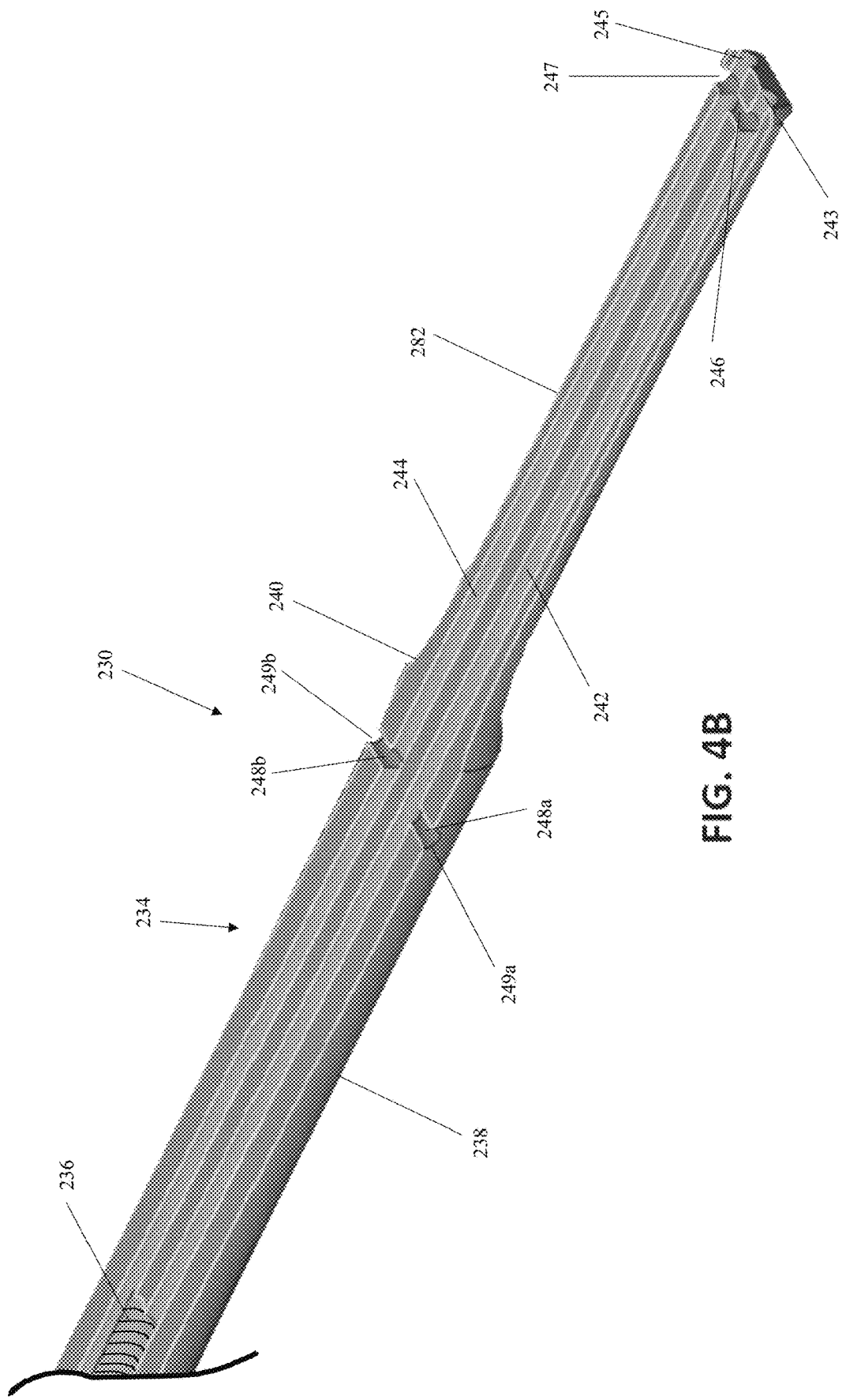
FIG. 4B is a longitudinal, cross-sectional view of a distal body of the waveguide of FIG. 4A illustrating an internal flow path formed therein.

With particular reference to FIGS. 4A and 4B, distal body 234 includes a base 238 and blade 282 extending distally from base 238. Base 238 and blade 282 may be integrally formed from a single piece of material or may be separately formed and subsequently attached to one another (permanently or removably). Base 238 defines a generally cylindrical-shaped configuration, although other configurations are also contemplated. Blade 282 extends distally from base 282. Blade 282 may define a substantially linear configuration (as shown), may define a curved configuration, or may define any other suitable configuration, e.g., straight and/or curved surfaces, portions, and/or sections; one or more convex and/or concave surfaces, portions, and/or sections; etc. With respect to curved configurations, blade 282, more specifically, may be curved in any direction relative to jaw 284 (FIG. 1), for example, such that the distal tip of blade 282 is curved towards jaw 284 (FIG. 1), away from jaw 284 (FIG. 1), or laterally (in either direction) relative to jaw 284 (FIG. 1). Further, blade 282 may be formed to include multiple curves in similar directions, multiple curves in different directions within a single plane, and/or multiple curves in different directions in different planes. In addition, although one configuration of blade 282 is described and illustrated herein, it is contemplated that blade 282 may additionally or alternatively be formed to include any suitable features, e.g., a tapered configuration, various different cross-sectional configurations along its length, cut-outs, indents, edges, protrusions, straight surfaces, curved surfaces, angled surfaces, wide edges, narrow edges, and/or other features. In aspects, blade 282 defines a pair of relatively narrow generally convex opposed surfaces and a pair of relatively broad generally planar opposed surfaces, although other configurations are also contemplated. One of the narrow surfaces may be positioned to oppose jaw 284 (FIG. 1), one of the broad surfaces may be positioned to oppose jaw 284 (FIG. 1), or blade 282 and/or jaw 284 (FIG. 1) may be relatively rotatable to position a desired surface in opposition to jaw 284 (FIG. 1). A transition region 240 defining a gradual (or more gradual) transition between base 238 and blade 282 may also be provided.

Distal body 234 may be formed from a solid material into which the various lumens detailed below are formed, although other configurations are also contemplated. Distal body 234, more specifically, includes first and second longitudinal lumens 242, 244 extending in substantially parallel, spaced-apart relation to one another through at least a portion of base 238 and blade 282. Longitudinal lumens 242, 244 communicate with distal apertures 243, 245, respectively, defined through a distal face of blade 282. Longitudinal lumens 242, 244 may be formed within distal body 234 during manufacture of distal body 234 (e.g., as part of an extrusion process or other suitable formation process) or may be formed subsequent to manufacture of distal body 234 (e.g., via drilling). In either configuration, longitudinal lumens 242, 244 extend through the distal face of blade 282 proximally through blade 282 and at least a portion of base 238 to closed or open proximal ends. Alternatively, in configurations where distal body 234 is removable from proximal body 232 (FIG. 4A), longitudinal lumens 242, 244 may be formed within distal body 234 through a proximal end portion of base 238 (or of waveguide 230) to or through the distal face of blade 282. In aspects, threaded bore 236 of base 238 communicates with open proximal ends of longitudinal lumens 242, 244. In such aspects, threaded engagement of threaded plug 233 of proximal body 232 (see FIG. 4A) within threaded bore 236 of base 238 of distal body 234 to attach proximal and distal bodies 232, 234 with one another also serves to seal the proximal ends of longitudinal lumens 242, 244 closed (either by itself or with a seal, e.g., a grommet, o-ring, gasket, sealant, overmold, etc., disposed between proximal and distal bodies 232, 234, e.g., pressed distally to bottom out within threaded bore 236). In other configurations, longitudinal lumens 242, 244 communicate with one or more internal lumens (e.g., a single lumen or dedicated lumens corresponding to each longitudinal lumen 242, 244) defined within proximal body 232 and extending at least partially therethrough to closed or closable proximal ends of the internal lumen(s) of proximal body 232. In aspects, such internal lumens of proximal body 232 extend to the proximal end of proximal body 232 and are sealed closed (themselves or with a seal) via engagement of proximal body 232 of waveguide 230 with transducer 320 (FIG. 2), e.g., via the threaded engagement therebetween.

Continuing with reference to FIGS. 4A and 4B, a distal transverse lumen 246 is defined at least partially through blade 282 at a distal end portion of blade 282, e.g., within approximately 15% of a length of blade 282 from the distal end thereof, in other aspects within approximately 10%, and in still other aspects, within approximately 5%. Distal transverse lumen 246 may be formed within blade 282 via drilling, e.g., forming a distal transverse aperture 247 disposed on one side of blade 282, or in any other suitable manner. Distal transverse lumen 246 extends transversely across one of the longitudinal lumens 242, 244 into communication with the other longitudinal lumen 242, 244. In this manner, distal transverse lumen 246 establishes communication between longitudinal lumens 242, 244 within the distal end portion of blade 282. Distal transverse lumen 246 may not extend completely through blade 282, e.g., such that a single distal transverse aperture 247 is formed, or may extend completely therethrough, e.g., such that a pair of opposed distal transverse apertures 247 is formed. Distal transverse lumen 246 may extend in substantially perpendicular orientation relative to longitudinal lumens 242, 244 or at an angle relative thereto.

Base 238 of distal body 234 of waveguide 230 defines a pair of proximal transverse lumens 248a, 248b therethrough, although it is also contemplated that proximal transverse lumens 248a, 248b be defined within proximal body 232 of waveguide 230 (in configuration wherein longitudinal lumens 242, 244 communicate with corresponding lumens defined through at least a portion of proximal body 232). Proximal transverse lumens 248a, 248b extend from transverse apertures 249a, 249b on opposing sides of base 238 into communication with longitudinal lumens 242, 244, respectively, or may be disposed on the same side of base 238 and extend into communication with respective longitudinal lumens 242, 244. Longitudinal lumens 242, 244 may terminate at proximal transverse lumens 248a, 248b or may extend proximally therebeyond. Proximal transverse lumens 248a, 248b may be formed via drilling through base 238 or in any other suitable manner. Proximal transverse lumens 248a, 248b may extend only partially through base 238 so as to maintain isolation between longitudinal lumens 242, 244 within base 238, or may extend completely through base 238 whereby the undesired apertures formed thereby are sealed closed during manufacturing, e.g., according to any of the aspects detailed herein. Whether by initial formation or subsequent sealed closure, proximal transverse lumens 248a, 248b each communicate with one of the longitudinal lumens 242, 244 but not the other longitudinal lumen 242, 244. Proximal transverse lumens 248a, 248b may be transversely aligned with one another or longitudinally offset relative to one another and either or both may extend in substantially perpendicular orientation relative to longitudinal lumens 242, 244 or at angles relative thereto.

Figure 5:
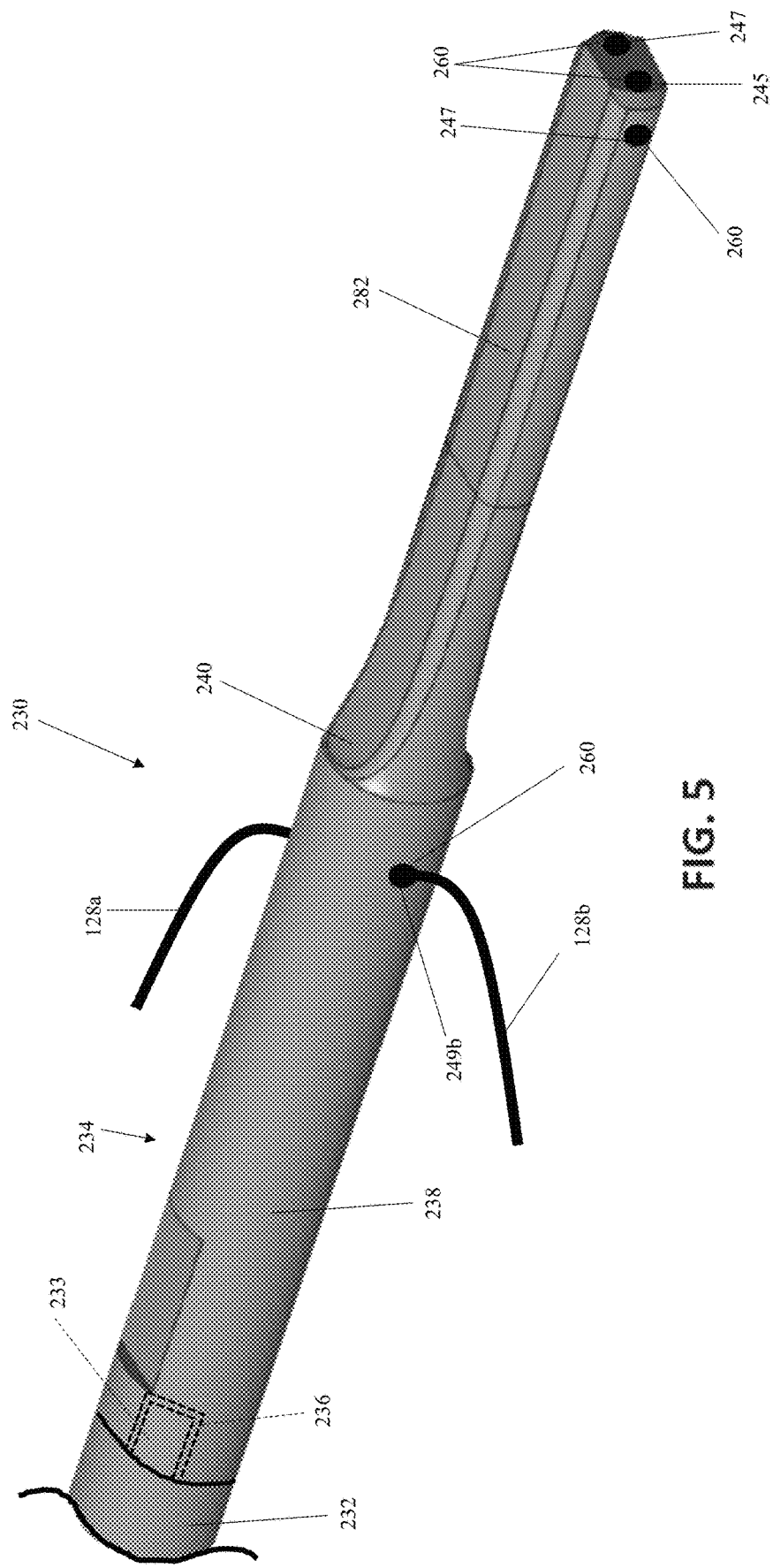
FIG. 5 is a perspective view of the distal portion of the waveguide of FIG. 4A assembled with inflow and return conduits connected thereto and the fluid flow path sealed closed.

Referring also to FIG. 5, during manufacturing, in order to define a closed fluid circuit from cooling system 120, through waveguide 230, and back to cooling system 120 (see FIG. 2), inflow and return conduits 128a, 128b are coupled, in fluid communication, with longitudinal lumens 242, 244, respectively, and the various apertures 243, 245, 247, 249a, 249b defined through waveguide 230 are sealed to inhibit escape of fluid from the closed fluid circuit. Although the fluid circuit from cooling system 120 through waveguide 230 and back to cooling system 120 is closed, cooling system 120 may itself define an open-loop configuration (e.g., wherein supply fluid and return fluid are separate and return fluid is not re-circulated), a closed-loop configuration (e.g., wherein return fluid is re-circulated as supply fluid), or a semi-closed loop configuration (e.g., wherein some return fluid is re-circulated while other return fluid is not re-circulated). Further still, in other configurations, one or more apertures 243, 245, 247, 249a, 249b defined through waveguide 230 are sealed closed while one or more other apertures 243, 245, 247, 249a, 249b defined through waveguide 230 remain open to enable the direction of fluid from waveguide 230 in a particular manner or manners in an open-loop system, e.g., to function as an aspirator and/or suction device.

Inflow and return conduits 128a, 128b may extend to or at least partially through transverse apertures 249a, 249b to enable the delivery of inflow fluid through proximal transverse aperture 249a, proximal transverse lumen 248a, and into longitudinal lumen 242, from longitudinal lumen 242 to longitudinal lumen 244 at the distal end portion of blade 282 via distal transverse lumen 246, and to enable the return of return fluid from longitudinal lumen 244, through proximal transverse lumen 248b and transverse aperture 249b to return conduit 128b. Inflow conduit 128a and/or return conduit 128b may, interiorly and/or exteriorly relative to waveguide 230, be oriented substantially perpendicularly relative to longitudinal lumens 242, 244, respectively, or may be angled relative thereto. Additionally or alternatively, as noted above, proximal transverse lumens 248a, 248b may be angled or substantially perpendicular relative to longitudinal lumens 242, 244. Angling inflow conduit 128a and/or return conduit 128b and/or angling either or both proximal transverse lumens 248a, e.g., in a proximally-angled manner, may facilitate inflow and outflow of fluid to and from longitudinal lumens 242, 244, respectively, although other configurations are also contemplated. In configurations where inflow and return conduits 128a, 128b extend at least partially into proximal transverse lumens 248a, 248b, respectively, the ends of inflow and return conduits 128a, 128b may be cut at an angled, chamfered, or otherwise asymmetrically configured to facilitate fluid flow in a desired manner, e.g., distally from inflow conduit 128a through longitudinal lumen 242 and/or proximally through longitudinal lumen 244 into return conduit 128b.

Referring still to FIGS. 4A-5, apertures 243, 245, 247, 249a, 249b may be closed via corresponding plugs 260. Plugs 260 may be similar or different from one another and may sealingly close apertures 243, 245, 247, 249a, 249b in similar or different manners. One or more of plugs 260 may be configured, for example, as a rod, e.g., a titanium rod or other rod of similar of different material from distal body 234 of waveguide 230, that is inserted into the corresponding aperture 243, 245, 247, 249a, 249b and welded therein to sealingly close the aperture 243, 245, 247, 249a, 249b. In such aspects, lost wax, depth gauge, or other suitable fixturing may be utilized to retain the rod in pace during welding. In aspects, one or more of plugs 260 may be formed from, for example, a high temperature polymer, rubber, or metal and, in these or other aspects, may be welded, thermally interference fit, soldered (wherein the plugs are formed wholly from the solder material or wherein a plug of different material is soldered), brazed, or otherwise secured in position within the corresponding aperture 243, 245, 247, 249a, 249b to sealingly close the corresponding aperture 243, 245, 247, 249a, 249b.

The plug 260 configured to sealingly close apertures 243, 245, in aspects, may be joined via a connector such that plugs 260 are together inserted into corresponding apertures 243, 245 and secured therein (in any manner detailed herein or any other suitable manner, and with plugs 260 formed from any suitable material such as any of those detailed herein). Such a plug 260 may define a substantially U-shaped configuration and be inserted from the exterior of waveguide 230. Alternatively, such a plug 260 may include an O-ring (itself or together with plug portions extending therefrom) or other seal connector, e.g., a gasket, that is inserted distally through lumen 242, 244 to seal apertures 243, 245 (and, in some aspects, also aperture 247) closed.

One or more of plugs 260 may be overmolded from the interior or exterior of the corresponding aperture 243, 245, 247, 249a, 249b to sealingly close the corresponding aperture 243, 245, 247, 249a, 249b. One or more of plugs 260 may be separately formed and then inserted (from the interior or exterior) and sealed within the corresponding aperture 243, 245, 247, 249a, 249b, or may be formed within the corresponding aperture 243, 245, 247, 249a, 249b, e.g., via filling the corresponding aperture with material via overmolding, casting, brazing, soldering, etc. from the interior or exterior thereof. One or more of plugs 260 may be configured as a set screw or other threaded element and/or one or more of apertures 243, 245, 247, 249a, 249b may include threading to enable sealed engagement via threading (itself (e.g., via pipe thread sealing) or with an additional seal or seal material) of the one or more plugs 260 within the corresponding aperture(s) 243, 245, 247, 249a, 249b, from the interior or exterior thereof.

In configurations wherein longitudinal lumens 242, 244 define open proximal ends, the open proximal ends may be collectively or individually plugged according to any of the aspects detailed above or in any other suitable manner. Further, with respect to the plugs 260 for apertures 249a, 249b, inflow and outflow conduits 128a, 128b, respectively, may extend through the plugs 260, be defined within the plugs 260, form the plugs 260, be surrounded by the plugs 260, or be otherwise configured relative to the plugs 260 such that the plugs 260 seal apertures 249a, 249b and inflow and outflow conduits 128a, 128b, respectively, to inhibit escape of fluid from the system while allowing fluid flow between waveguide 230 and inflow and outflow conduits 128a, 128b. Combinations of any two or more of the above-noted plug configurations are also contemplated as are other configurations to facilitate sealed closure of some or all apertures 243, 245, 247, 249a, 249b.

With general reference to FIGS. 1-5, in use, upon activation of cooling, cooling system 120 is configured to pump fluid, using the one or more fluid pumps 122, from fluid reservoir 124, through inflow conduit 128a, proximal transverse lumen 248a, distally through longitudinal lumen 242, from longitudinal lumen 242 to longitudinal lumen 244 at the distal end portion of blade 282 via distal transverse lumen 246, proximally through longitudinal lumen 244, through transverse lumen 248b, through outflow conduit 128b, and back to fluid reservoir 124. In this manner, cooling fluid is circulated substantially entirely along the length of blade 282 to facilitate cooling blade 282. The cooling fluid may be saline, water, or other suitable fluid.

Figure 6B:
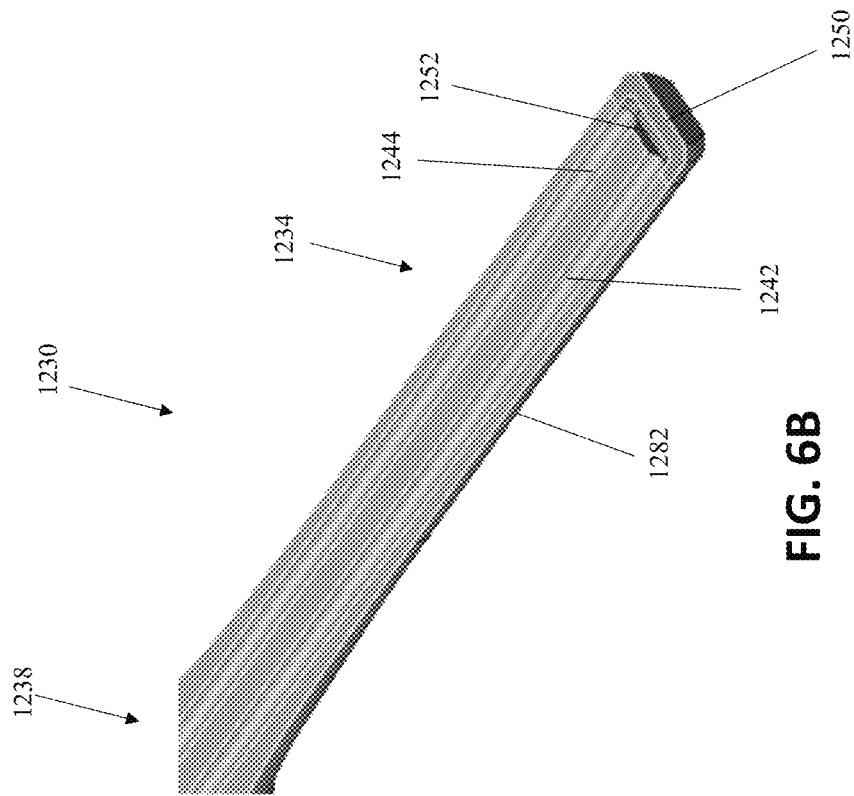
FIGS. 6A and 6B are perspective and longitudinal, cross-sectional views, respectively, of a distal portion of another waveguide provided in accordance with the present disclosure.
Figure 6A:
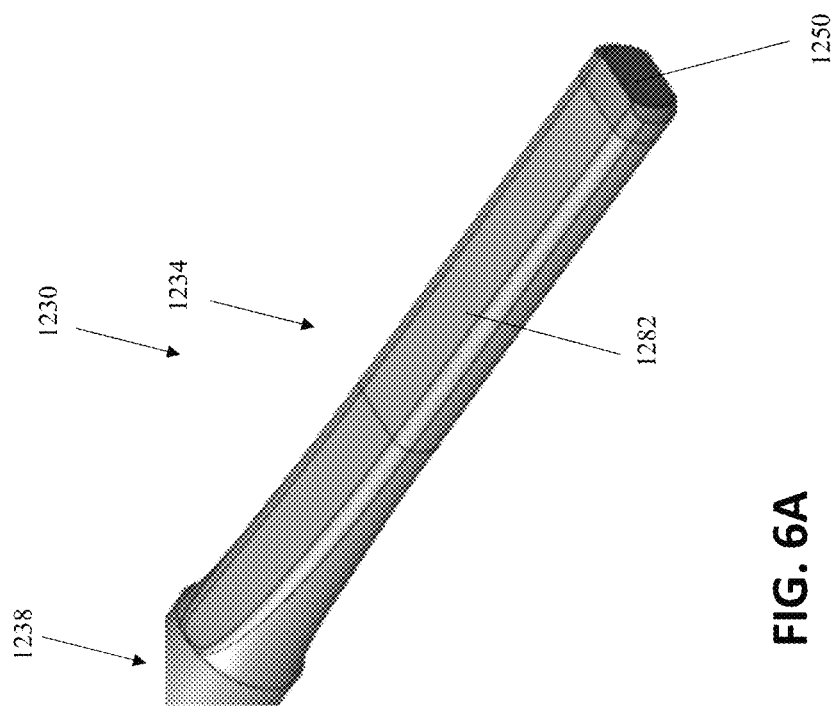

Turning to FIGS. 6A-6B, a distal body 1234 including a blade 1282 of another waveguide 1230 provided in accordance with aspects of the present disclosure is shown. Except as explicitly contradicted below, waveguide 1230 may be configured similarly to and include any of the features of waveguide 230 (FIGS. 1, 2, 4A, and 4B). Thus, the following description will focus on differences between waveguide 1230 and waveguide 230 (FIGS. 1, 2, 4A, and 4B) while similarities are only summarily described or omitted entirely.

Distal body 1234 of waveguide 1230 includes a base 1238 and blade 1282 extending distally from base 1238. Distal body 1234 further includes first and second longitudinal lumens 1242, 1244 extending in substantially parallel, spaced-apart relation relative to one another through at least a portion of base 1238 and blade 1282 to open distal ends. A cap 1250 defining a connector lumen 1252 is welded, soldered, or otherwise secured to the distal end of blade 1282 to thereby define a distal tip of blade 1282. Cap 1250 may be formed from the same material as blade 1282 or a different material. Upon securing cap 1250 to the distal end of blade 1282, connector lumen 1252 establishes communication between the open distal ends of longitudinal lumens 1242, 1244 and otherwise seals off the fluid flow path, inhibiting the escape of fluid from within distal body 1234. Thus, cooling fluid can be pumped distally through distal body 1234 via one of longitudinal lumens 1242, 1244 and can return proximally through distal body 1234 via connector lumen 1252 and the other longitudinal lumen 1242, 1244 to thereby cool distal body 1234 of waveguide 1230. With respect to distal body 1234, a transverse lumen need not be provided towards distal ends of longitudinal lumens 1242, 1244.

Figure 7:
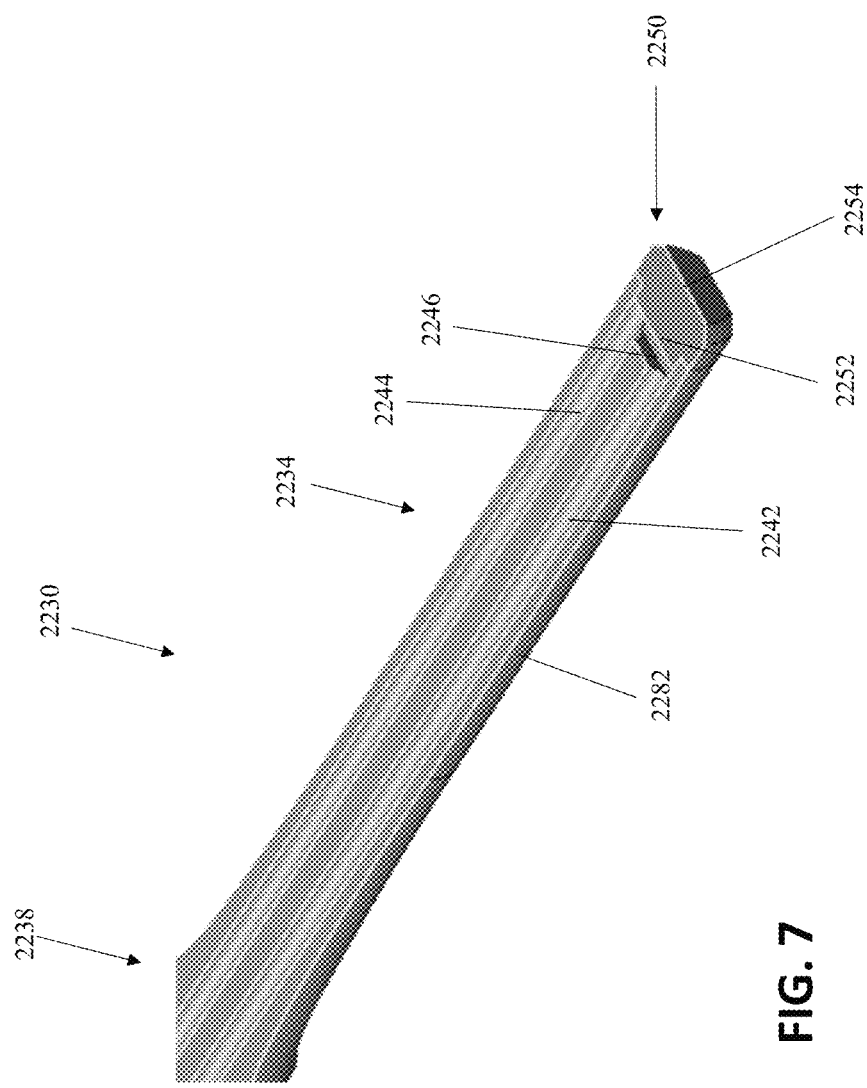
FIG. 7 is a longitudinal, cross-sectional view of a distal portion of still another waveguide provided in accordance with the present disclosure.

With reference to FIG. 7, a distal body 2234 including a blade 2282 of another waveguide 2230 provided in accordance with aspects of the present disclosure is shown. Distal body 2234 is similar to and may include any of the features of distal body 1234 (FIGS. 6A and 6B) except as explicitly contradicted below.

Distal body 2234 of waveguide 2230 includes a base 2238 and blade 2282 extending distally from base 2238. Distal body 2234 further includes first and second longitudinal lumens 2242, 2244 extending in substantially parallel, spaced-apart relation relative to one another through at least a portion of base 2238 and blade 2282. Longitudinal lumens 2242, 2244 terminate at and communicate with a transverse lumen 2246 disposed at the distal end of blade 2282 and in communication with an open distal end thereof. Thus, lumens 2242, 2244, 2246 all communicate with the open distal end of blade 2282.

A cap 2250 including a base 2252 and a head 2254 is welded, soldered, or otherwise secured to the distal end of blade 2282 to thereby define a distal tip of blade 2282 with base 2252 extending at least partially into the open distal end of blade 2282 and head 2254 abutting the distal face(s) of blade 2282. Upon securing cap 2250 to the distal end of blade 2282 in this manner, the open distal end of blade 2282 is sealed closed while still maintaining a fluid flow path between longitudinal lumens 2242, 2244 via transverse lumen 2246. Thus, cooling fluid can be pumped distally through distal body 2234 via one of longitudinal lumens 2242, 2244 and can return proximally through distal body 2234 via transverse lumen 2246 and the other longitudinal lumen 2242, 2244 to thereby cool distal body 2234 of waveguide 2230. Base 2252 of cap 2250 facilitates proper alignment and orientation of cap 2250 relative to blade 2282 upon welding or otherwise securing cap 2250 to blade 2282.

Figure 8:
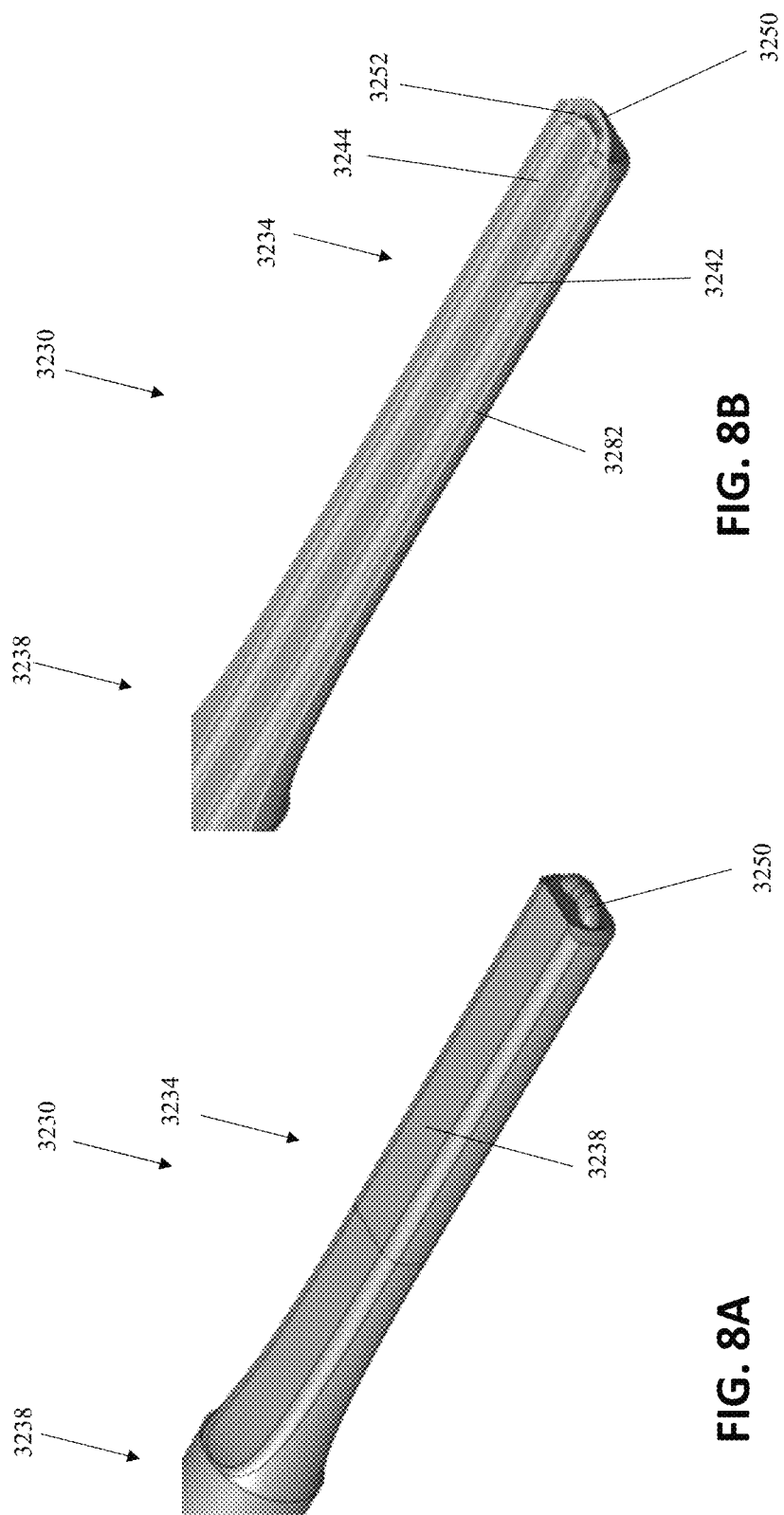
FIGS. 8A and 8B are perspective and longitudinal, cross-sectional views, respectively, of a distal portion of yet another waveguide provided in accordance with the present disclosure.

Referring to FIGS. 8A and 8B, a distal body 3234 including a blade 3282 of another waveguide 3230 provided in accordance with aspects of the present disclosure is shown. Distal body 3234 is similar to and may include any of the features of distal body 1234 (FIGS. 6A and 6B) except as explicitly contradicted below.

Rather than providing a cap 1250 as detailed above with respect to distal body 1234 (see FIGS. 6A and 6B), distal body 3234 includes a bent pipe 3250 (curved, angled, and/or otherwise bent) defining a lumen 3252 therethrough secured, e.g., welded, soldered, or otherwise secured, to the distal end of blade 3282 such that lumen 3252 establishes communication between the open distal ends of longitudinal lumens 3242, 3244 and otherwise seals off the fluid flow path, inhibiting the escape of fluid from distal body 3234. Thus, cooling fluid can be pumped distally through distal body 3234 via one of longitudinal lumens 3242, 3244 and can return proximally through distal body 3234 via lumen 3252 and the other longitudinal lumen 3242, 3244 to thereby cool distal body 3234 of waveguide 3230.

With general reference to FIGS. 6A-8B, in aspects, cap 1250, cap 2250, and/or pipe 3250 may define features to facilitate tissue treatment. For example, cap 1250, cap 2250, and/or pipe 3250 may define angled, rounded, curved, and/or other suitable configurations to facilitate, for example, performing otomies, blunt dissection, and/or other surgical tasks with or without ultrasonic energy.

Figures 9, 10:
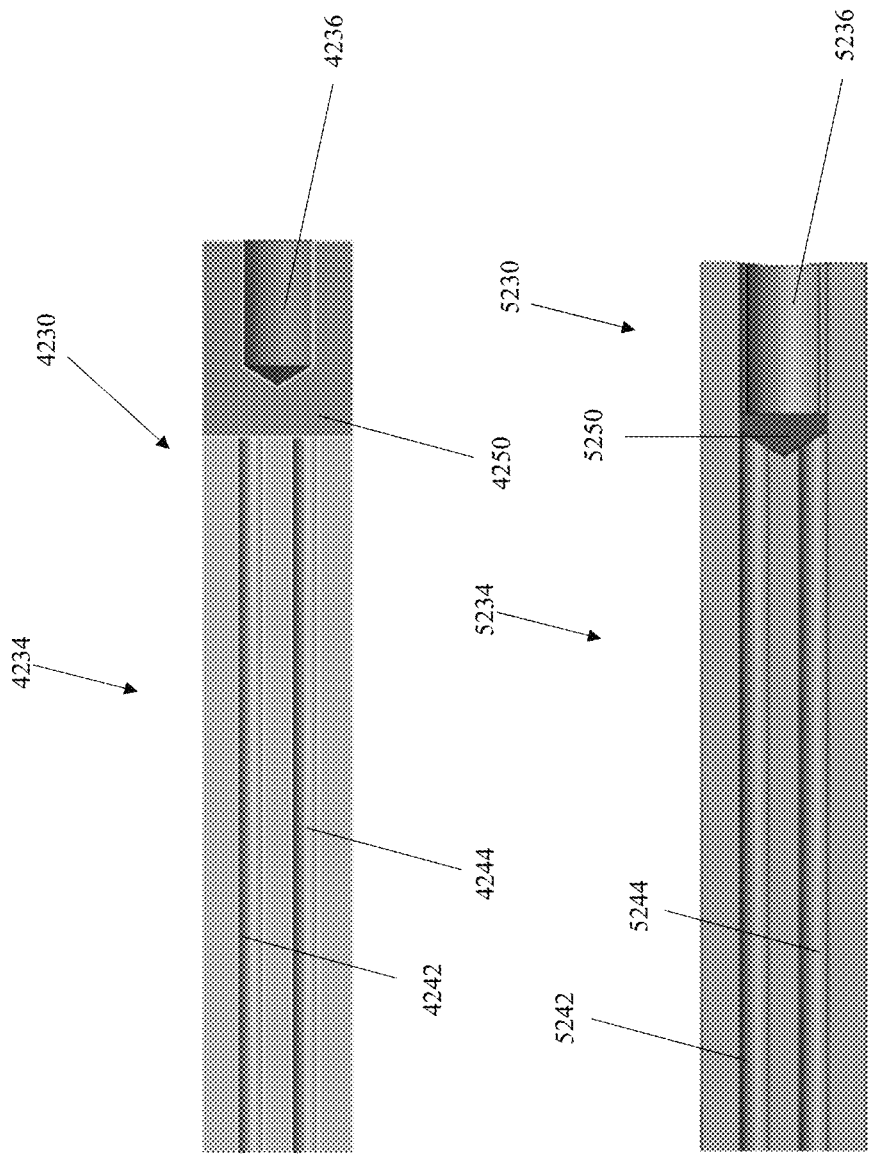
FIGS. 9 and 10 are longitudinal, cross-sectional views of proximal portions of still yet other waveguides provided in accordance with the present disclosure.

Turning to FIGS. 9 and 10, proximal end portions of the distal bodies 4234, 5234 of still other waveguides 4230, 5230 provided in accordance with aspects of the present disclosure are shown. Except as explicitly contradicted below, waveguides 4230, 5230 may be configured similarly to and include any of the features of waveguide 230 (FIGS. 1, 2, 4A, and 4B), any of the other waveguides detailed herein, and/or any other suitable waveguide. Thus, the following description will focus on differences between waveguides 4230, 5230 and the above-detailed waveguides, e.g., waveguide 230 (FIGS. 1, 2, 4A, and 4B), while similarities are only summarily described or omitted entirely.

Referring to FIG. 9, distal body 4234 of waveguide 4230 defines longitudinal lumens 4242, 4244 extending at least partially therethrough. Longitudinal lumens 4242, 4244 define open proximal ends open to the proximal end of distal body 4234. Distal body 4234 of waveguide 4230 further includes a connector body 4250 secured, e.g., welded, soldered, or otherwise secured, to the proximal end of distal body 4234. Connector body 4250 may be formed from the same or a different material as distal body 4234 and, upon securing connector body 4250 to the proximal end of distal body 4234, seals closed the proximal ends of longitudinal lumens 4242, 4244. Connector body 4250 may further include a proximal bore 4236 to enable threaded or other suitable engagement of the proximal body (not shown, see proximal body 232 (FIG. 4A)) of waveguide 4230 within proximal bore 4236 to thereby secure the proximal body and distal body 4234 with one another (via connector body 4250 therebetween) to enable ultrasonic energy transmission therealong.

With reference to FIG. 10, distal body 5234 of waveguide 5230 defines longitudinal lumens 5242, 5244 extending at least partially therethrough and a proximal bore 5236 defined therein at the proximal end thereof. The proximal ends of longitudinal lumens 5242, 5244 communicate with proximal bore 5236. A plug 5250 is secured within proximal bore 5236 at the open proximal ends of longitudinal lumens 5242, 5244 to seal off the proximal ends of longitudinal lumens 5242, 5244. Plug 5250 may be formed from any suitable material similar or different from that of waveguide 5230 and may be welded, soldered, adhered, molded, compression-fit (such as where plug 5250 is formed from a resilient material), threaded, or otherwise secured within proximal bore 5236. Plug 5250 occupies only a portion of proximal bore 5236 to enable threaded or other suitable engagement of the proximal body (not shown, see proximal body 232 (FIG. 4A)) of waveguide 5230 within proximal bore 5236 to thereby secure the proximal body and distal body 5234 with one another to enable ultrasonic energy transmission therealong.

While several aspects and features of the disclosure are detailed above and shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular configurations. Those skilled in the art will envision other modifications within the scope and spirit of the claims appended hereto.

What is claimed is:

1. An ultrasonic surgical system, comprising:
   an ultrasonic waveguide body comprising:
      a proximal waveguide body adapted to connect to an ultrasonic transducer, and
      a distal waveguide body including a blade and defining first and second longitudinal lumens extending through at least a portion of a length of the distal waveguide body, the distal waveguide body extending distally from the proximal waveguide body;
   a distal transverse lumen that intersects and interconnects the first and second longitudinal lumens;
   a first proximal transverse lumen extending from a first proximal transverse aperture within the ultrasonic waveguide body transversely through a portion of the ultrasonic waveguide body to intersect the first longitudinal lumen, wherein the first proximal transverse aperture is in a first side of the ultrasonic waveguide body;
   a second proximal transverse lumen extending from a second proximal transverse aperture within the ultrasonic waveguide body transversely through a portion of the ultrasonic waveguide body to intersect the second longitudinal lumen, wherein the second proximal transverse aperture is in a second side of the ultrasonic waveguide body, and the second proximal transverse aperture is transversely aligned with the first proximal transverse aperture; and
   inflow and outflow conduits fluidly coupled with the first and second proximal transverse apertures, respectively, to enable inflow of fluid into the first longitudinal lumen and outflow of fluid from the second longitudinal lumen, respectively,
   wherein the distal waveguide body is releasably engageable with the proximal waveguide body.

2. The ultrasonic surgical system according to claim 1, wherein first and second proximal transverse aperture plugs form a seal between the inflow and outflow conduits and the first and second proximal transverse apertures, respectively.

3. The ultrasonic surgical system according to claim 1, wherein the distal waveguide body includes a base and a blade extending distally from the base, the blade defining opposed narrow surfaces and opposed broad surfaces.

4. The ultrasonic surgical system according to claim 3, wherein at least a portion of the distal transverse lumen is disposed within 10% of a length of the blade from a distal end of the blade.

5. The ultrasonic surgical system according to claim 1, further comprising:
   a cooling system configured to pump cooling fluid through the inflow conduit into the first longitudinal lumen and/or pump cooling fluid through the second longitudinal lumen into the outflow conduit;
   a housing at least partially supporting the cooling system; and
   an elongated assembly extending distally from the housing, the elongated assembly including the ultrasonic waveguide body.

6. The ultrasonic surgical system according to claim 5, wherein the housing further supports an ultrasonic transducer configured to produce ultrasonic energy for transmission along the ultrasonic waveguide body.

7. The ultrasonic surgical system according to claim 6, wherein the housing further supports an ultrasonic generator configured to produce an ultrasonic drive signal for driving the ultrasonic transducer, and a battery configured to power the ultrasonic generator.

8. An ultrasonic surgical system, comprising:
an ultrasonic waveguide body defining first and second longitudinal lumens extending through at least a portion of a length of the ultrasonic waveguide body;
a distal transverse lumen defined within the ultrasonic waveguide body transversely through at least a portion of the ultrasonic waveguide body to intersect and interconnect the first and second longitudinal lumens, wherein the distal transverse lumen extends from a distal transverse aperture and wherein a distal transverse aperture plug closes the distal transverse aperture to inhibit escape of fluid therethrough;
a first proximal transverse lumen extending from a first proximal transverse aperture within the ultrasonic waveguide body transversely through a portion of the ultrasonic waveguide body to intersect the first longitudinal lumen;
a second proximal transverse lumen extending from a second proximal transverse aperture within the ultrasonic waveguide body transversely through a portion of the ultrasonic waveguide body to intersect the second longitudinal lumen; and
inflow and outflow conduits fluidly coupled with the first and second proximal transverse apertures, respectively, to enable inflow of fluid into the first longitudinal lumen and outflow of fluid from the second longitudinal lumen, respectively.

9. The ultrasonic surgical system according to claim 8, wherein the first and second longitudinal lumens extend proximally from first and second distal face apertures defined within a distal face of the ultrasonic waveguide body, and wherein at least one distal face aperture plug closes the first and second distal face apertures to inhibit escape of fluid therethrough.

10. An ultrasonic surgical system, comprising:
a proximal waveguide body adapted to connect to an ultrasonic transducer;
a distal waveguide body including a blade and defining first and second longitudinal lumens extending through at least a portion of a length of the distal waveguide body, the distal waveguide body extending distally from the proximal waveguide body;
a distal transverse lumen defined within the distal waveguide body transversely through at least a portion of the distal waveguide body to intersect and interconnect the first and second longitudinal lumens;
a first proximal transverse lumen extending from a first proximal transverse aperture within the distal waveguide body transversely through a portion of the distal waveguide body to intersect the first longitudinal lumen;
a second proximal transverse lumen extending from a second proximal transverse aperture within the distal waveguide body transversely through a portion of the distal waveguide body to intersect the second longitudinal lumen; and
inflow and outflow conduits fluidly coupled with the first and second proximal transverse apertures, respectively, to enable inflow of fluid into the first longitudinal lumen and outflow of fluid from the second longitudinal lumen, respectively,
wherein the distal waveguide body is releasably engageable with the proximal waveguide body.

11. The ultrasonic surgical system according to claim 10, wherein engagement of the proximal and distal waveguide bodies closes proximal ends of the first and second longitudinal lumens.

12. An ultrasonic surgical system, comprising:
an ultrasonic waveguide body defining first and second longitudinal lumens extending through at least a portion of a length of the ultrasonic waveguide body;
a distal transverse lumen defined within the ultrasonic waveguide body transversely through at least a portion of the ultrasonic waveguide body to intersect and interconnect the first and second longitudinal lumens, wherein the distal transverse lumen is at least partially formed via a distal cap defining a distal tip of the ultrasonic waveguide body;
a first proximal transverse lumen extending from a first proximal transverse aperture within the ultrasonic waveguide body transversely through a portion of the ultrasonic waveguide body to intersect the first longitudinal lumen;
a second proximal transverse lumen extending from a second proximal transverse aperture within the ultrasonic waveguide body transversely through a portion of the ultrasonic waveguide body to intersect the second longitudinal lumen; and
inflow and outflow conduits fluidly coupled with the first and second proximal transverse apertures, respectively, to enable the inflow of fluid into the first longitudinal lumen and the outflow of fluid from the second longitudinal lumen, respectively.

13. A method of manufacturing an ultrasonic surgical system, comprising:
forming first and second longitudinal lumens through at least a portion of a length of an ultrasonic waveguide body;
forming a distal transverse lumen transversely through at least a portion of the ultrasonic waveguide body to intersect and interconnect the first and second longitudinal lumens;
forming first and second proximal transverse lumens transversely through a portion of the ultrasonic waveguide body to intersect the first and second longitudinal lumens, respectively;
plugging apertures formed from the formation of the first and second longitudinal lumens; and
plugging an aperture formed from the formation of the distal transverse lumen.

14. The method according to claim 13, further comprising fluidly connecting an inflow conduit with the first proximal transverse aperture.

15. The method according to claim 13, further comprising fluidly connecting an outflow conduit with the second proximal transverse aperture.

16. The method according to claim 13, further comprising attaching the ultrasonic waveguide body, as a distal waveguide body, to a proximal waveguide body.

17. The method according to claim 16, wherein the attaching closes proximal ends of the first and second longitudinal lumens.

18. The method according to claim 13, further comprising:
coupling the first and second proximal transverse lumens with inflow and outflow conduits, respectively, associated with a cooling system including at least one pump and a fluid reservoir.

19. The method according to claim 13, wherein forming the distal transverse lumen includes securing a cap to a distal end of the ultrasonic waveguide body to define a distal tip thereof.

* * * * *